(12) United States Patent
Jensen et al.

(10) Patent No.: US 7,635,845 B2
(45) Date of Patent: Dec. 22, 2009

(54) IR SENSOR, ESPECIALLY A $CO_2$ SENSOR

(75) Inventors: Jens Moeller Jensen, Horsens (DK);
Mohamed Yahia Benslimane, Nordborg (DK)

(73) Assignee: Danfoss A/S, Nordborg (DK)

( * ) Notice: Subject to any disclaimer, the term of this patent is extended or adjusted under 35 U.S.C. 154(b) by 330 days.

(21) Appl. No.: 11/629,420

(22) PCT Filed: Jun. 10, 2005

(86) PCT No.: PCT/DK2005/000381

§ 371 (c)(1),
(2), (4) Date: Dec. 12, 2006

(87) PCT Pub. No.: WO2005/121751

PCT Pub. Date: Dec. 22, 2005

(65) Prior Publication Data

US 2008/0283753 A1   Nov. 20, 2008

(51) Int. Cl.
*G01J 5/02* (2006.01)
(52) U.S. Cl. .............. 250/339.01; 250/338.5; 250/343; 250/349
(58) Field of Classification Search ............ 250/338.5, 250/339.01, 343–346
See application file for complete search history.

(56) References Cited

U.S. PATENT DOCUMENTS

| | | | | |
|---|---|---|---|---|
| 4,785,184 A | * | 11/1988 | Bien et al. | 250/343 |
| 5,005,947 A | | 4/1991 | Sibilo et al. | 350/252 |
| 5,081,998 A | | 1/1992 | Yelderman et al. | 128/719 |
| 5,162,658 A | | 11/1992 | Turner et al. | 250/554 |
| 5,306,913 A | * | 4/1994 | Noack et al. | 250/338.5 |
| 5,610,400 A | * | 3/1997 | Weckstrom | 250/345 |
| 5,612,676 A | | 3/1997 | Plimpton et al. | 340/578 |
| 5,672,874 A | | 9/1997 | Fujii et al. | 250/343 |
| 5,800,360 A | | 9/1998 | Kisner et al. | 600/532 |
| 5,995,008 A | * | 11/1999 | King et al. | 340/578 |
| 6,369,716 B1 | | 4/2002 | Abbas et al. | 340/632 |
| 6,392,234 B2 | | 5/2002 | Dickmann | 250/338.3 |

(Continued)

FOREIGN PATENT DOCUMENTS

DE   43 19 567 A1   12/1994

(Continued)

*Primary Examiner*—David P Porta
*Assistant Examiner*—Casey Bryant
(74) *Attorney, Agent, or Firm*—McCormick, Paulding & Huber LLP

(57) ABSTRACT

An IR sensor (1), especially a $CO_2$ sensor, is described, having a filter arrangement (6), downstream of which there is arranged a detector arrangement (7), and an evaluating device (8) which is connected to the detector arrangement (7), the filter arrangement (6) having a first filter (9) and a second filter (10), which are configured as bandpass filters and each have a passband and of which the first filter (9) allows passage of a predetermined IR band and the second filter (10) does not, and the detector arrangement having two detectors (14, 15), each of which is associated with a filter (9, 10). The objective is to simplify the use of such an IR sensor. For that purpose, the passband of one filter (10) is arranged within the passband of the other filter (9) and the evaluating device (8) forms the difference of the signals (S1, S2) of the detectors (14, 15) and normalises it to the signal (S1) of a detector (14).

7 Claims, 2 Drawing Sheets

U.S. PATENT DOCUMENTS

| | | | |
|---|---|---|---|
| 2003/0120434 A1 | 6/2003 | DiDomenico et al. | 702/22 |
| 2003/0147080 A1* | 8/2003 | Sarkis et al. | 356/437 |

FOREIGN PATENT DOCUMENTS

| | | |
|---|---|---|
| GB | 930698 | 7/1963 |
| GB | 2 176 889 A | 1/1987 |
| WO | 97/25613 | 7/1997 |
| WO | 00/55602 | 9/2000 |

* cited by examiner

IR SENSOR, ESPECIALLY A CO₂ SENSOR

CROSS REFERENCE TO RELATED APPLICATIONS

This application is entitled to the benefit of and incorporates by reference essential subject matter disclosed in International Patent Application No. PCT/DK2005/000381 filed on Jun. 10, 2005 and German Patent Application No. 10 2004 028 433.4 filed Jun. 14, 2004.

FIELD OF THE INVENTION

The invention relates to an IR sensor, especially a $CO_2$ sensor, having a filter arrangement, downstream of which there is arranged a detector arrangement, and an evaluating device which is connected to the detector arrangement, the filter arrangement having a first filter and a second filter, which are configured as bandpass filters and each have a passband and of which the first filter allows passage of a predetermined IR band and the second filter does not, and the detector arrangement has two detectors, each of which is associated with a filter.

BACKGROUND OF THE INVENTION

The invention is described below with reference to an IR sensor for IR-absorbing gases, but can also be used for other purposes, as will be explained hereinbelow.

Such a sensor, which is configured as a gas sensor, is known, for example, from U.S. Pat. No. 5,081,998 A. An IR radiation source is provided therein, which acts upon a total of four detectors by way of a filter arrangement. The filter arrangement has two filters having different pass characteristics. A first filter has a passband for IR radiation that is absorbed by $CO_2$. That filter is therefore also referred to as a "$CO_2$ filter". The detectors arranged downstream are designated $CO_2$ detectors. The other filter has a passband different therefrom which serves for determining a reference quantity. The detectors arranged downstream of that reference filter are referred to as reference detectors. Between the IR source and the two filters there is arranged a third filter which is referred to as a natural density filter and overlaps half of the first filter and half of the second filter. Accordingly, one of the two $CO_2$ detectors and one of the reference detectors receives only IR radiation that has passed both through the natural density filter and through either the $CO_2$ filter or the reference filter. In the evaluating device, the difference of the output signals of the two $CO_2$ detectors and the difference of the two reference detectors is formed. The two differences are then divided by one another. Such a $CO_2$ sensor is required, for example, for determining $CO_2$ in a patient's breath so as to be better able to monitor the patient during anaesthesia.

Another field of use for gas sensors, especially $CO_2$ sensors, is described in U.S. Pat. No. 6,369,716 B1. The $CO_2$ sensor therein is used for determining the $CO_2$ content (carbon dioxide content) in a room in order to be able to control the room climate with the aid of that measured quantity.

The $CO_2$ concentration in a room should be between 800 ppm and 1200 ppm, because higher concentrations can give rise to fatigue symptoms. The natural concentration in built-up areas is normally about 400 ppm. With the aid of a $CO_2$ sensor it is possible to determine how much fresh air needs to be supplied in order to achieve a desired $CO_2$ concentration. The same considerations apply also to other gases for which a specific content should not be exceeded, for example CO (carbon monoxide) or the like.

As mentioned above, the invention is described below with reference to the measurement of $CO_2$, but it is also suitable for use for other gases.

One way of measuring $CO_2$ in the air is based on gas-phase-based sensors in which non-dispersive infrared spectroscopy (NDIR) is used. Such a method of determining the $CO_2$ content proceeds on the basis that $CO_2$ absorbs infrared radiation, that is to say the content of IR radiation in a specific, narrowly defined wavelength range is a quantity that can be used for determining the $CO_2$ concentration.

A disadvantage of such sensors is that they have a relatively high power requirement. The arrangement known from U.S. Pat. No. 5,081,998 A requires a source of radiation which, in any case for prolonged use, makes it unsuitable for battery-operated use. Furthermore, such an IR source generally requires a certain heating-up period, so that without a degree of prior preparation it is not always possible to carry out measurements when desired.

BRIEF SUMMARY OF THE INVENTION

The problem underlying the invention is to simplify the use of an IR sensor.

That problem is solved by a gas sensor of the kind mentioned at the beginning wherein the passband of one filter is arranged within the passband of the other filter and the evaluating device forms the difference of the signals of the detectors and normalises it to the signal of a detector.

That configuration makes it possible to evaluate substantially more IR radiation. The IR radiation is therefore not divided into two separate ranges, with each detector detecting only one range. Instead, one detector detects IR radiation having a pre-set spectral range, which also includes, for example, the absorption spectrum of the gas being determined, here $CO_2$. The other detector detects an IR spectrum from a sub-range thereof, which does not include the absorption spectrum of the gas being determined. The sensitivity of the sensor is thus considerably increased, that is to say only relatively low demands are made for the supply of IR radiation to the sensor. Because the difference between the output signals of the detectors is formed, an interfering signal, for example background noise or the like, is eliminated. The normalisation of the difference to the output signal of a detector enables fluctuations in the intensity of the IR radiation to be compensated. It is also possible to use more than two sensors with a correspondingly greater number of filters, the individual pass ranges then overlapping accordingly. With such a sensor it is also possible to obtain other information, for example relating to temperature, to movement in the room, to the number of persons in the room, etc. Because it is possible to detect substantially more radiation, the power consumption can be reduced, so that the necessary power can also be supplied by a battery. That in turn gives greater freedom in terms of local mounting and use. The sensor can transmit its signals wirelessly.

The passband of the first filter is preferably larger than the passband of the second filter. Accordingly, the first filter, in addition to including the spectral range allowed to pass by the second filter, also includes the spectral range in which IR radiation is absorbed.

The two filters preferably have a common cut-off wavelength. That simplifies evaluation. The difference between the output signals of the detectors can then readily be formed without additional calculation steps being necessary. The cut-off wavelengths are the wavelengths that define, that is to say limit, the passbands. They are referred to as "start wavelength" and "end wavelength".

It is preferred here that both filters have the same start wavelength. The "start wavelength" is the wavelength from which the filters allow passage of radiation. The "same" start wavelength need not be identical in the mathematical sense. Customary tolerances, for example 5%, are entirely permissible. Although such tolerances do influence the measurement result, that influence is acceptable.

Both filters are preferably formed by filter elements in series, one filter element being the same for both filters and defining a cut-off wavelength. The two filter elements are therefore arranged one after the other in the radiation direction, that is to say between the source(s) for IR radiation and the detectors. It is also possible to configure the filter arrangement so that the "start wavelength" is defined by the filter element which is the same for both filters, and the "end wavelength" which limits the passband is defined by the two other filter elements. That is a simple measure by means of which the passbands of the two filters can be fixed with comparatively high accuracy.

The first filter advantageously has a passband that is from 0.3 to 0.7 μm greater than the passband of the second filter. It is desirable for the first filter to cover basically only a relatively narrow wavelength range or spectral range of the IR spectrum, namely the range in which IR radiation is absorbed by $CO_2$. The range indicated is sufficient for this. The risk that absorption by other gases will have an adverse effect on the measurement result and falsify that result is kept small.

It is preferable here for the first filter to have a passband in the range of from 3.6 to 4.5 μm and the second filter to have a passband in the range of from 3.6 to 4.0 μm. Generally it can be said that the common spectral range is approximately half the size of the spectral range allowed to pass by the first filter. In dependence upon the gases or other quantities being detected, those spectral ranges can of course also be shifted. It has been found, however, that those wavelength ranges are advantageous for $CO_2$.

In an especially preferred configuration, the sensor uses the natural IR radiation from the environment. There is therefore no need for a source of radiation that needs a separate power supply and accordingly has a certain power requirement. IR radiation is generally present everywhere, even when there is no incident sunlight. In principle every body has a certain amount of thermal radiation. Because it is then possible to do without an IR radiation source, the "measurement range" is also broadened, that is to say it is possible to monitor relatively large areas of a room for the content of the gas in question. This facilitates the monitoring and establishment of a "personal room climate" or the indoor air quality. It is unnecessary first to conduct the air in the room to a sensor where it is passed between the source of IR radiation and the detectors with upstream filters. It is sufficient for the sensor to be arranged at a point in the room where it can, as it were, "survey" the volume of air to be monitored. In that case, the gas sensor can, as it were, detect the averaged gas concentration in a simple way. The sensor therefore determines an average value, which, particularly for the personal room climate, constitutes a substantially better measurement result. Of course, it is also possible to use the sensor to improve the technology of sensors that operate with lamps or other means of lighting. When natural or ambient IR radiation is used, the energy of the light means can be reduced. That results in longer maintenance intervals and a longer service life.

The evaluating device preferably normalises the difference to the signal of the first detector. In other words, for normalisation the signal containing the $CO_2$ content is used. That procedure results in a somewhat greater dynamic performance.

The filters preferably contain $CaF_2$, germanium or silicon. The silicon preferably has an anti-reflective coating in order to improve transmission.

BRIEF DESCRIPTION OF THE DRAWINGS

The invention will be described hereinbelow with reference to a preferred exemplary embodiment in conjunction with the drawings.

DETAILED DESCRIPTION OF THE INVENTION

Figure 1:
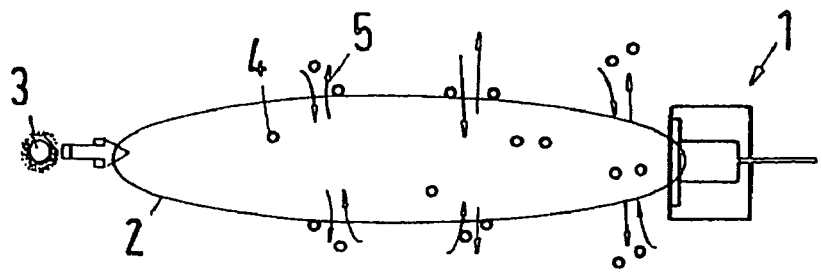
FIG. 1 is a diagrammatic view for explaining the operating principle of the present invention.

FIG. 1 shows a diagrammatic view of a gas sensor 1 for determining the $CO_2$ content (carbon dioxide content) in a measurement region 2. The measurement region may be, for example, a room or the portion of a room in which the personal room climate is to be regulated. A sun symbol 3 represents a natural IR source. The sun symbol 3 serves here merely for explanation purposes. The gas sensor 1 also operates in the absence of sunlight, because in principle virtually any body radiates heat and thus generates IR rays.

A large number of $CO_2$ molecules are present in the measurement region 2, the $CO_2$ molecules being represented herein by small circles. The gas molecules 4 absorb IR rays in a specific spectral range, as represented by arrows 5. The greater the concentration of $CO_2$, the lower the energy in a specific spectral range that can be detected in the gas sensor 1.

Figure 4:
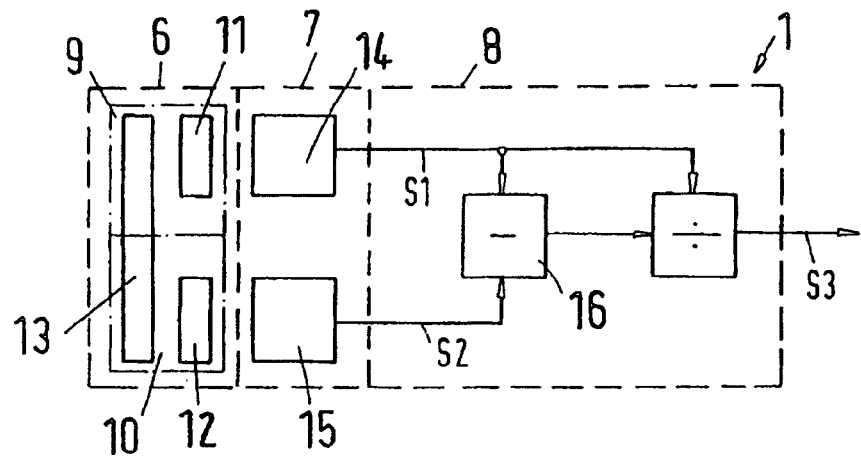
FIG. 4 is a block circuit diagram for explaining the structure of the gas sensor.

FIG. 4 shows, in diagrammatic form, a block circuit diagram for explaining the structure of the gas sensor 1. The gas sensor 1 has a filter arrangement 6, a detector arrangement 7 and an evaluating device 8. Further details, such as the housing, fixing means or the like, are not shown herein.

Figure 2:
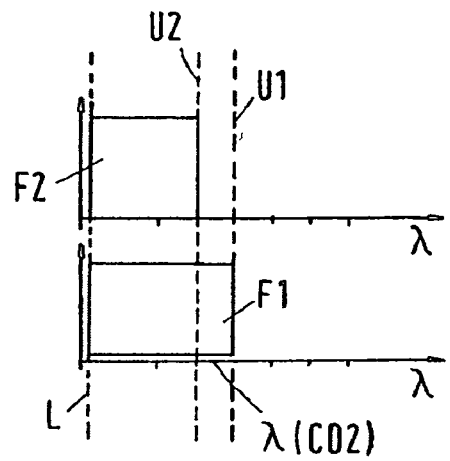
FIG. 2 shows, in diagrammatic form, two passbands of two filters.

The filter arrangement has a first filter 9 and a second filter 10. The two filters have different pass characteristics, which are shown in FIG. 2. The first filter has a passband F1. The second filter has a passband F2. The two passbands F1, F2 begin at the same lower limit L, but have different upper limits, the pass range F1 having an upper limit U1 and the pass range F2 having an upper limit U2. The distance between the upper limit U1 of the first passband F1 and the upper limit U2 is in the order of magnitude of from about 0.3 to about 0.7 μm, for example 0.5 μm.

In the range in which the passband F1 of the first filter 9 is greater than the passband F2 of the second filter 10, there is a spectral range λ ($CO_2$) in which IR radiation is absorbed by $CO_2$. That spectral range is located at about from 4.2 to 4.3 μm. Accordingly, the upper limit U1 of the first passband F1 can be arranged at about 4.5 μm, the upper limit U2 of the second passband F2 at about 4.0 μm and the lower limit L, which is common to both passbands F1, F2, at 3.6 μm.

This can be implemented in a relatively simple way by the first filter 9 having a first filter element 11 which defines the upper limit U1 of the passband F1. The second filter 10 has a second filter element 12 which defines the upper limit U2 of the second passband F2. For the two filters 9, 10 in common, a third filter element 13 is provided, which defines the lower limit L of the two passbands F1, F2. The third filter element 13 has an upper pass limit beyond the upper limit U1 of the passband F1 of the first filter 9. The first and the second filter elements have a lower pass limit which lies below the lower limit L of the third filter element 13.

Figure 3:
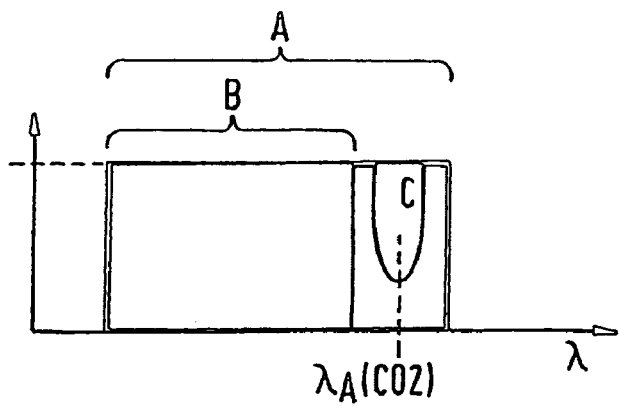
FIG. 3 shows, in diagrammatic form, the amount of energy that can be detected by detectors.

Accordingly, in the range of the first filter 9 the filter arrangement 6 allows passage of IR radiation having an energy indicated by reference letter A in FIG. 3. That energy is reduced by an amount C which is absorbed by $CO_2$. In the range of the second filter 10 the filter arrangement 6 allows passage of energy which is labelled with reference letter B in FIG. 3. That energy is virtually constant, because it is not affected by $CO_2$.

The different energies are then detected by the detector arrangement 7. The detector arrangement 7 has a first detector 14 which detects the IR radiation which passes through the first filter 9, and a second detector 15 which detects the IR radiation which passes through the second filter 10. The two detectors 14, 15 can be in the form of thermoelectric elements which are also known as "thermopiles". In dependence upon the IR radiation that occurs, each detector generates a voltage or a current, that is to say an electrical quantity, which is the greater the more IR radiation is incident. Accordingly, the first detector 14 generates a signal S1 and the second detector 15 generates a signal S2.

A thermopile sensor is obtainable, for example, from PerkinElmer Optoelectronics GmbH, D-65199 Wiesbaden, Germany.

Because, in a thermopile sensor, usually a temperature measurement is carried out (because the output signal varies with temperature), measurement of the temperature around the sensor has already been incorporated. As it is conceivable that the radiation temperature of the room is also obtainable by means of the sensor, it is possible on the basis of those two measurements simultaneously to obtain directly an operating temperature which can then be used for controlling the room temperature or something quite different.

In connection with IR it is also conceivable that measurement of a movement in the room is directly possible with the sensor, which can then be used, for example, for controlling a ventilating system, which, for example, is activated only in the event of a movement indicating that there is someone in the room. On the basis of various movement measurements it is also conceivable that it would be possible to estimate the number of people in the room, such an estimate also being usable for control purposes, so that the room temperature or the ventilation is controlled/modified in dependence upon the number of people in the room.

The two signals S1, S2 are supplied to the evaluating device 8, both signals containing an interfering component. It is assumed that the interfering component is substantially the same for both detectors 14, 15. Accordingly, this gives $$S1 = a(I_{CO_2} + I_n)$$

$$S2 = a(I_{ref} + I_n)$$

where $I_{CO_2}$ is the electrical quantity, for example the current or the voltage, containing the information relating to the IR radiation, while $I_{ref}$ is the reference quantity that is not affected by the IR radiation. In the case of $I_n$, the index n denotes noise. When the difference between S1 and S2 is formed, for which purpose a difference former 16 is shown diagrammatically, the following quantity is obtained:

$$S1 - S2 = a(I_{CO_2} - I_{ref})$$

in which the noise component has disappeared.

That difference S1−S2 is normalised to the output signal S1 of the first detector 14, so that a signal S3 is obtained.

$$S3 = \frac{S1 - S2}{S1} = \frac{a(I_{CO_2} - I_{ref})}{a(I_{CO_2} + I_n)}$$

Although that output signal S3 is in turn affected by the interfering value $I_n$, that interference is negligible. The information obtained relating to the $CO_2$ content of the measurement region 2 is very reliable, however.

Figure 5:
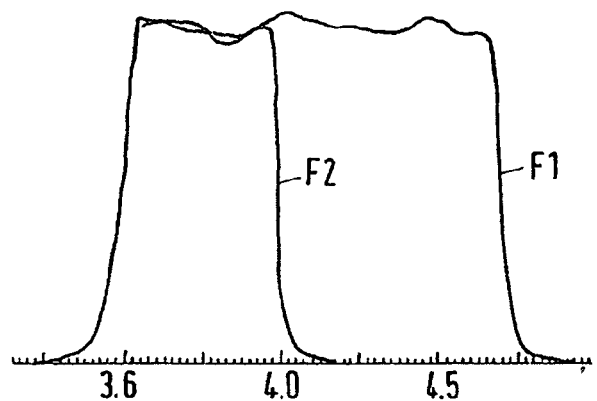
FIG. 5 shows, in diagrammatic form, the pass range of two filters.

FIG. 5 shows again the different pass ranges F1, F2 of the two filters 9, 10, from which the differences between the two pass ranges can clearly be seen.

Figure 6:
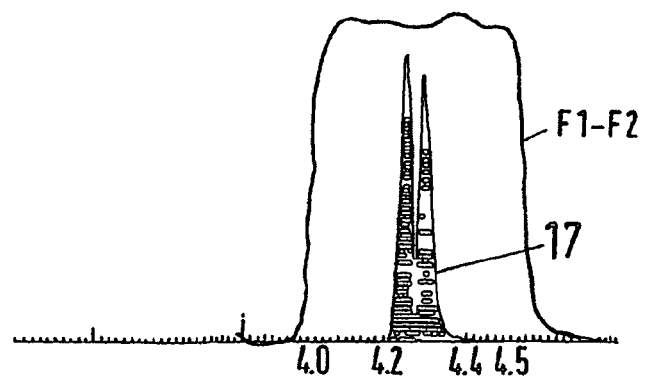
FIG. 6 is a diagrammatic view of a preliminary stage of an evaluation signal.

FIG. 6 shows the difference from the two pass ranges F1, F2 and, indicated therein, the absorption spectrum 17 for $CO_2$.

The gas sensor is able reliably to determine $CO_2$ concentrations in the range of from about 300 to about 1500 ppm.

When other gases are to be determined, for example nitrogen, nitric oxides, oxygen or CO, the passbands must be shifted accordingly. In every case, however, it should be ensured that the passbands overlap in order to allow the greatest possible energy yield to pass to the detectors 14, 15.

It is also possible for a collecting device, that is to say a device that gathers or focuses IR radiation, for example a collimator, to be arranged upstream of the sensor. That also improves the sensor.

It is also possible to use such a sensor directly for waste gas monitoring. For that purpose, it is installed in the chimney or exhaust. Particularly in the case of heating systems, combustion can then be controlled with the aid of the output signals of the sensor (or of a plurality of sensors).

While the present invention has been illustrated and described with respect to a particular embodiment thereof, it should be appreciated by those of ordinary skill in the art that various modifications to this invention may be made without departing from the spirit and scope of the present invention.

What is claimed is:

1. An IR sensor, especially a $CO_2$ sensor, having a filter arrangement, downstream of which there is arranged a detector arrangement, and an evaluating device which is connected to the detector arrangement, the filter arrangement having a first filter and a second filter, which are configured as bandpass filters and each have a passband and of which the first filter allows passage of a predetermined IR band and the second filter does not, and the detector arrangement having a first detector and a second detector, each of which is associated with one of the first filter and the second filter, the passband of the second filter being arranged within the passband of the the first filter and the evaluating device forming a difference of signals of the first detector and the second detector, wherein the first filter and second filter are formed by filter elements in series, one filter element being the same for both the first filter and the second filter and defining a common cut-off wavelength and the evaluating device normalising the difference of signals of the first detector and the second detector to the signal of one of the first detector and the second detector.

2. The IR sensor according to claim 1, wherein the two filters have the same start wavelength.

3. The IR sensor according to claim 1, wherein the first filter has a passband that is from 0.3 to 0.7 µm larger than the passband of the second filter.

4. The IR sensor according to claim 3, wherein the first filter has a passband in the range of from 3.6 to 4.5 µm and the second filter has a passband in the range of from 3.6 to 4.0 µm.

5. The IR sensor according to claim 1, wherein the IR sensor uses the natural IR radiation from the environment.

6. The IR sensor according to claim 1, wherein the evaluating device normalises the difference to the signal of the first detector.

7. The IR sensor according to claim 1, wherein the filters contain $CaF_2$, germanium or silicon.

* * * * *